United States Patent [19]

Foley et al.

[11] 3,993,837

[45] Nov. 23, 1976

[54] COMPLEX ORGANO SILICON COMPOUNDS

[75] Inventors: Kevin M. Foley, Hebron; Francesco M. Vigo, Heath, both of Ohio

[73] Assignee: Owens-Corning Fiberglas Corporation, Toledo, Ohio

[22] Filed: Apr. 4, 1975

[21] Appl. No.: 565,169

Related U.S. Application Data

[63] Continuation-in-part of Ser. No. 347,264, April 2, 1973, Pat. No. 3,899,524, and a continuation-in-part of Ser. No. 347,241, April 2, 1973, Pat. No. 3,931,266.

[52] U.S. Cl. .................................. 428/391; 428/392
[51] Int. Cl.² .......................................... B32B 9/00
[58] Field of Search .......... 428/268, 391, 273, 378, 428/392, 394, 266; 260/448.8 R, 348 SC

[56] References Cited
UNITED STATES PATENTS

| | | | |
|---|---|---|---|
| 2,649,396 | 8/1953 | Witt et al. | 428/391 |
| 3,591,408 | 7/1971 | Marzocchi et al. | 428/392 |
| 3,702,783 | 11/1972 | Hartlein | 428/392 |
| 3,944,707 | 3/1976 | Foley et al. | 428/392 |

*Primary Examiner*—James J. Bell
*Attorney, Agent, or Firm*—John W. Overman; Philip R. Cloutier

[57] ABSTRACT

A composition for use in the treatment of glass fibers and glass fibers treated therewith, wherein the composition is formulated to include an organo silicon compound in the form of an epoxy silane blended with an organo silicon compound containing a beta-chloroalkoxy group. The glass fibers treated with the composition can be used in the reinforcement of thermosetting resins and elastomeric materials.

32 Claims, No Drawings

COMPLEX ORGANO SILICON COMPOUNDS

This is a continuation-in-part of copending applications Ser. No. 347,264 now U.S. Pat. No. 3899524 and Ser. No. 347,241 now U.S. Pat. No. 3931266 both filed on Apr. 2, 1973.

This invention relates to size compositions, and more particularly to size compositions for use in the treatment of glass fibers to improve the bonding relationship between glass fibers and resinous plastics in the manufacture of glass fiber reinforced plastics.

The term "glass fibers," as used herein, is intended to refer to and include (1) continuous fibers formed by rapid attenuation of hundreds of streams of molten glass and to strands formed when such continuous glass fiber filaments are gathered together as they are being formed; and to yarns and cords formed by plying and/or twisting a number of strands together, and to woven and non-woven fabrics which are formed of such glass fiber strands, yarns or cords, and (2) discontinuous fibers formed by high pressure steam, air or other suitable attenuating force directed onto multiple streams of molten glass issuing from a glass melting bushing or from an orifice containing spinner, and to yarns that are formed when such discontinuous fibers are gathered together to form a sliver which is drafted into a yarn; and to woven and non-woven fabrics formed of such yarns of discontinuous fibers, and (3) combinations of such continuous and discontinuous fibers in strands, yarns, cords and fabrics formed thereof.

It is now standard practice in the manufacture of glass fiber-reinforced plastics to employ glass fibers which have been coated with an organo silicon compound in the form of an organo silane or its hydrolysis products (e.g., the corresponding silanols and/or polysiloxanes). The nature of the organo silicon compound employed depends somewhat on the particular plastic to be reinforced. For example, where the resin is a polyepoxide, the organo silicon compound is frequently an organo silane containing an epoxy group

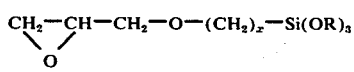  (1)

where x is an integer from 2 to 5 and R is an alkyl group containing 1 to 5 carbon atoms, or the corresponding hydrolysis products thereof. Where the resin is a polyester, the organo silicon compound frequently contains ethylenic unsaturation; the silane can be $$CH_2=CH-Si(OR)_3 \quad (2)$$

or more preferably

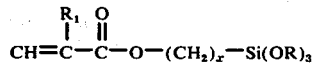  (3)

wherein $R_1$ is hydrogen or methyl.

While such silanes as well as their hydrolysis products are quite effective in promoting a secure bond between glass fibers and thermosetting plastics, they are quite expensive and therefore provide a significant contribution to the overall cost of manufacture of glass fiber reinforced plastics. Numerous attempts have been made to reduce the cost of such silanes, usually by replacing a portion of the epoxy- or acryloxyalkylsilanes with a less expensive silane. In U.S. Pat. No. 3,702,783 there is described a size composition which is formulated to contain a glycidoxyalkyl silane of the type described above and a methyltrialkoxy silane. However, the methyltrialkoxy silane is not significantly less expensive than the glycidoxyalkyl silane and, consequently, the organo silicon compounds proposed by the foregoing patent represent only marginal savings.

It is accordingly an object of the present invention to provide a size composition for use in the treatment of glass fibers to promote a secure bonding relationship between glass fibers and organic resins.

It is a more specific object of the invention to provide a size composition for use in the treatment of glass fibers for use as reinforcement for resinous plastics.

It is another object of the invention to provide glass fibers treated with the composition of this invention for use as reinforcement for plastics.

The concepts of the present invention reside in glass fibers which have been sized, preferably as they are formed, with a size composition formulated to include as the essential components an epoxy silane and an organo silicon compound characterized by one or more beta-haloalkoxy groups.

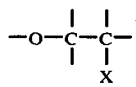

wherein X is halogen. It has been found that glass fibers having such a size coating on the surfaces thereof can be securely bonded to resinous plastics in the manufacture of glass fiber reinforced plastics.

As the epoxy silane, use can be made of epoxy silanes having the general formula

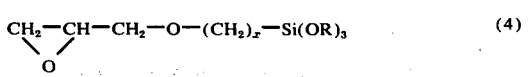  (4)

wherein x is an integer from 3 to 6 and R is lower alkyl (e.g., methyl, ethyl, propyl, isopropyl, etc.), or epoxy silanes of the formula

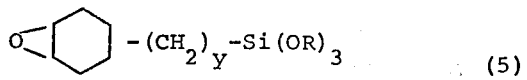  (5)

wherein y is an integer from 2 to 4, or the corresponding hydrolysis products such as the corresponding silanols and/or polysiloxanes.

Representative epoxy silanes gamma-glycidoxypropyltrimethoxy silane, gamma-glycidoxypropyltriethoxy silane, delta-glycidoxybutyltrimethoxy silane, 3,4-epoxycyclohexyethyltrimethoxy silane, etc.

The organo silicon compounds having the beta-haloalkoxy group employed in the practice of the invention are those described in copending applications Ser. No. 347,264 and Ser. No. 347,241, both of which were filed on Apr. 2, 1973, and the disclosures of which are incorporated herein by reference.

As is described in the foregoing copending applications, the complex organo silanes are prepared by reaction of various combinations of epoxides with a halosilane, and preferably a silicon tetrahalide. Epoxides used in the preparation of such silanes include alkylene oxides and the following:

[1] Epoxides of the formula

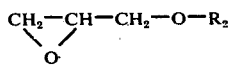  (6)

wherein $R_2$ is an aryl group such as phenyl or phenyl substituted with an amino group, a halogen group, an alkyl group; alkyl containing 1 to 20 carbon atoms and substituted derivatives thereof; an alkenyl group containing 2 to 8 carbon atoms (e.g., vinyl, allyl, etc.); styrene oxide; a group having the formula

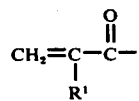  (7)

wherein R' is hydrogen or methyl. Illustrative of such epoxides are phenyl glycidyl ether, cresyl glycidyl ether, allyl glycidyl ether, glycidyl acrylate, glycidyl methacrylate, a mixture of n-octyl and n-decyl glycidyl ethers (Epoxide No. 7 from Procter and Gamble) and a mixture of n-dodecyl and n-tetradecyl glycidyl ethers (Epoxide No. 8 from Procter and Gamble). [2] Epoxides of the formula

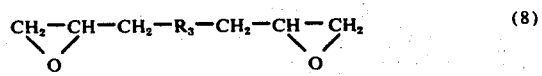  (8)

wherein $R_3$ is a divalent organic radical such as alkylene containing 1 to 10 carbon atoms; alkylene-oxyalkylene containing 2 to 20 carbons; oxyalkyleneoxy containing 1 to 10 carbon atoms; oxyalkylene-oxyalkyleneoxy containing 2 to 20 carbon atoms; divalent aromatic groups such as a group of the formula

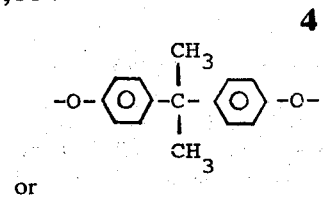  (9)

or

  (10)

A number of such epoxides are commercially avialable from Dow and Ciba and include the following:

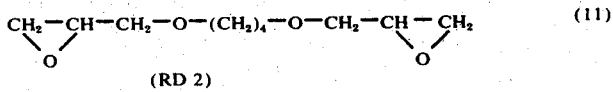  (11)

(RD 2)

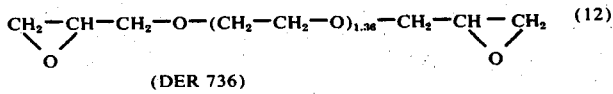  (12)

(DER 736)

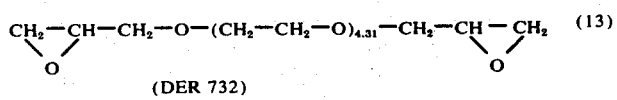  (13)

(DER 732)

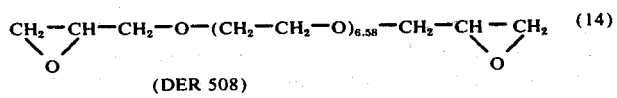  (14)

(DER 508)

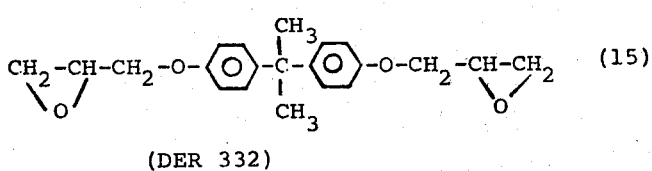  (15)

(DER 332)

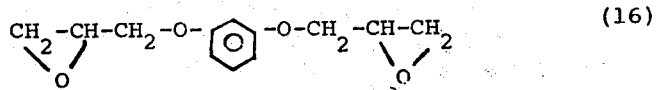  (16)

(ERE 1359)

[3] Cycloalkane epoxides, including the following:

  (17)

(RD or ERL 4206)

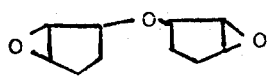  (18)

(ERR 4205)

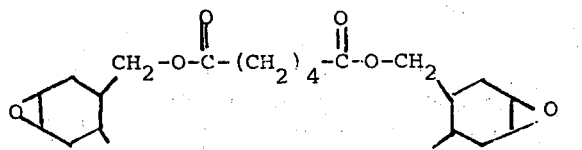

(ERR 4289)  (19)

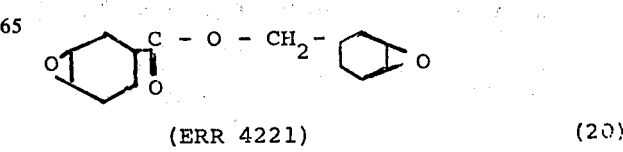

(ERR 4221)  (20)

In accordance with one embodiment of copending application Ser. No. 347,264, the organo silicon compounds are prepared by reaction of from 1 to 3 epoxide equivalents of the alkylene oxide and at least 0.5 and up to 3 epoxide equivalents of the epoxide containing a functional group per mole of the silicon tetrahalide. As used herein, the term "epoxide equivalent" refers to the number of moles of the epoxide times the number of epoxide groups per molecule. Thus, this reaction may be illustrated by the following:

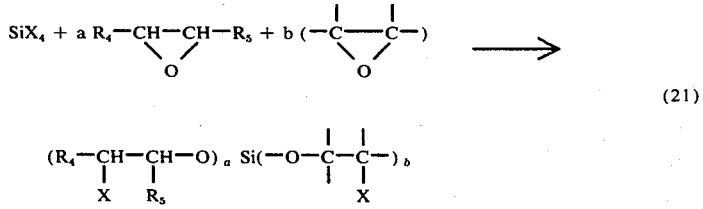

(21)

wherein X represent halogen, $R_4$ is hydrogen or $C_1$ to $C_4$ alkyl (e.g., methyl, ethyl, propyl, etc.), and $R_5$ is hydrogen or $C_1$ to $C_4$ alkyl, and preferably hydrogen, a represents the epoxide equivalent of the alkylene oxide and b represents the epoxide equivalent of the epoxide containing a functional group

(22)

In actual practice, the reaction product produced is a mixture of compounds which can be utilized as such without the need to separate specific compounds contained in the reaction product.

However, compounds contained in the reaction mixture can be, if desired, separated from the mixture by known techniques, such as fractional distillation, liquid chromatography, etc., to yield the substantially pure compounds. Such compounds frequently depend upon the epoxide equivalents employed, that is, the values of "a" and "b". For example, when the reaction mixture contains about 2 to 3 epoxide equivalents of the alkylene oxide and about 1 to 2 epoxide equivalents of the epoxide containing the functional group, the reaction product includes the following compounds:

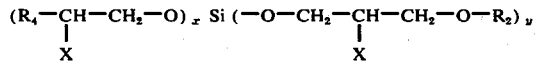

(23)

wherein X is an integer from 2 to 3 and y is an integer from 1 to 2, and wherein x is 3 and y is 1 and where X, $R_3$ and $R_4$ are as described above, as well as the corresponding derivatives where the epoxide is a cyclohexane epoxide.

Where the epoxide containing the functional group includes two or more epoxide groups, it is generally preferred that the equivalents of the alkylene oxide a be at least 2.2 and preferably at least 2.5 to avoid polymer formation which leads to gelling of the reaction product.

In preparing the reaction mixtures of the present invention, the reactants are contacted in the liquid phase. An inert organic solvent can be employed, if desired, but is not essential to the practice of the invention. The reaction temperature is not critical as the reaction generally takes place spontaneously and evolves heat. Best results are usually achieved when the reaction temperature is maintained below 100° C, such as within the range of 0° to 100° C.

When the epoxide containing the functional group as described above contains two or more epoxide groups, it is frequently preferred that the alkylene oxide be added to the halosilane prior to the time that the diepoxide is added to the reaction mixture. This procedure has the advantage that the reaction of alkylene oxide with the silicon tetrahalide is quite exothermic and thus raises the temperature of the reaction medium to a level suitable for addition of the epoxide containing the functional grouping.

Where the epoxide containing the functional group is a monoepoxide, the alkylene oxide or the monoepoxide can be added to the reaction mixture before the other, or they may be added simultaneously.

Where the reaction mixture contains two or more equivalents of an epoxide containing two or more epoxide groups per molecule, the reaction product includes compounds in which one of the epoxide groups in the functional epoxide remains unreacted with the silicon tetrahalide. For example, when the functional epoxide is one of those defined by [3] above, the reaction

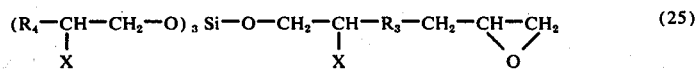

(25)

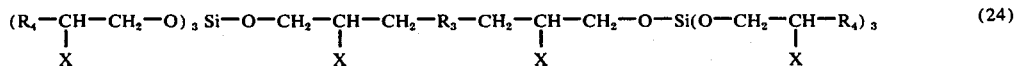

(24)

where $R_3$, $R_4$ and X are as described above.

In accordance with yet another embodiment of the invention, the halosilane employed in the reaction can contain one or more organo groups attached directly to the silicon atom through a carbon-to-silicon bond. In the preferred practice of this embodiment of the invention, the halosilane is of the formula $$(R_7)_n SiX_{(4-n)} \qquad (26)$$

wherein $R_7$ is an organic group containing 1 to 20 carbon atoms, n is an integer from 1 to 2 and X is halogen and preferably chlorine or bromine.

$R_7$ is preferably alkyl containing 1 to 20, and preferably 1 to 6 carbon atoms (e.g., methyl, ethyl, propyl, isopropyl, lauryl, etc.); alkenyl containing 2 to 20 and preferably 2 to 6 carbon atoms (e.g., vinyl, allyl, 3-butenyl, 4-pentenyl, etc.), cycloalkyl, such as cyclopentyl, cyclohexyl, etc., phenyl, as well as substituted derivatives thereof.

Where the organo halosilanes described above are reacted with an alkylene oxide and an epoxide containing a functional group as described above, it is preferred to employ from 1 to 2.5 epoxide equivalents or moles of the alkylene oxide per mole of the halosilane and from 0.5 to 3 epoxide equivalents of the epoxide containing the functional group per mole of the halosilane. Where the latter epoxide contains two epoxide groups and $n = 1$, it is desirable to employ at least 1.2 and preferably at least 1.5 epoxide equivalents of the alkylene oxide to minimize gel formation.

As is the case in the embodiments described above, the reaction product is usually in the form of a mixture of compounds. However, compounds which can be separated from the reaction products include:

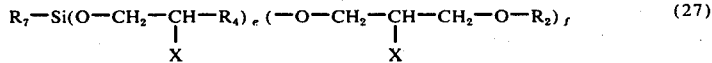

where $R_7$, $R_4$, $R_2$ and X are as described above and e is an integer from 1 to 2, and f is an integer from 1 to 2, with the total of e and f being equal to 3 where n is 1, and to 2 where n is 2;

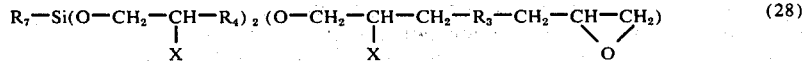

and/or

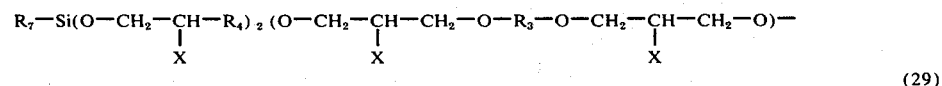

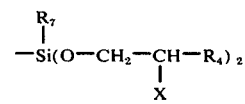

If desired, in the practice of this embodiment of the invention, the reaction can be carried out using a monoepoxide containing a functional group alone. This reaction frequently produces specific compounds but can also result in mixtures. Compounds produced include the following types:

Representative of specific compounds include the following:

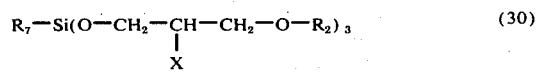

($CH_2=CHSiCl_3$ 1 mole; allyl glycidyl ether 3 epoxide equivalents)

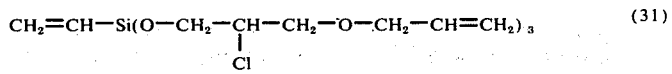

($CH_2=CHSiCl_3$ 1 mole; glycidyl acrylate 3 epoxide equivalents)

In accordance with one embodiment of copending application Ser. No. 347,241, the organo silicon compounds are prepared by reaction of from 1 to 3 epoxide equivalents of the monoepoxide and at least 0.5 and up to 3 epoxide equivalents of another epoxide containing a functional group per mole of the silicon tetrahalide. As used herein, the term "epoxide equivalent" refers to the number of moles of the epoxide times the number of epoxide groups per molecule.

For example, use can be made of a monoepoxide containing another functional group and a diepoxide as described above. This reaction can be illustrated by way of the following equations:

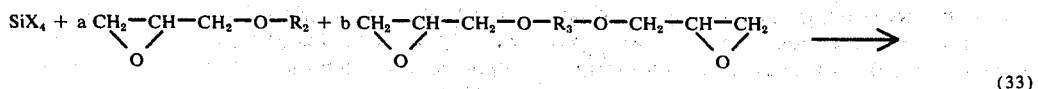

(33)

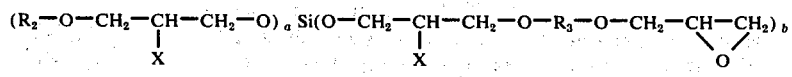

and

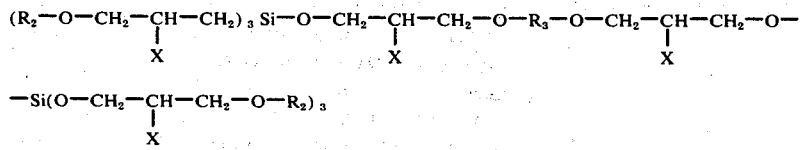

(34)

wherein X represents halogen, a represents the epoxide equivalent of the monoepoxide and b represents the epoxide equivalent of the diepoxide. In actual practice, the reaction product produced is a mixture of compounds which can be utilized as such without the need to separate specific compounds contained in the reaction product.

However, compounds contained in the reaction mixture can be, if desired, separated from the mixture by known techniques such as fractional distillation, liquid chromatography, etc., to yield substantially pure compounds.

It has been found that in the reaction mixture, a should be at least 2.2, and preferably at least 2.5, to avoid polymer formation which causes gelling of the product. Thus, a is within the range of 2.2 to 3.5 and b is within the range of 0.5 to 1.8. It has also been found that where the reaction mixture contains 2 or more epoxide equivalents of the diepoxide, the compounds which predominate in the reaction mixture have the general formula

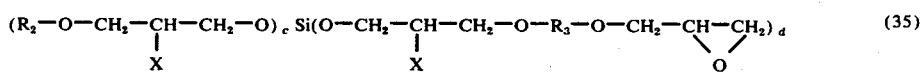

(35)

wherein $c$ is within the range of 2.0 to 3 and $d$ is within the range of 1 to 2.0. Most frequently, $c$ is 3 and $d$ is 1.

Where, however, use is made of less than 2 epoxide equivalents of the diepoxide, the product of the reaction includes compounds containing no free epoxy groups; these compounds have the general formula

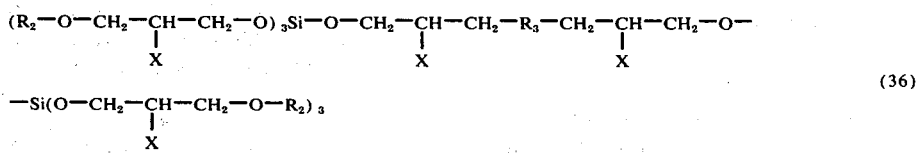

(36)

It will be observed that in all of the compounds specifically described above, each bond to the silicon atom contains a beta-haloalkoxy group. As indicated above, it is believed that such groupings impart improved stability to the compounds.

In accordance with another concept, the reaction is carried out with 0.5 to 2.5 moles of an alkylene oxide in addition to 0.5 to 2.5 epoxide equivalents of monoepoxide and the diepoxide. In this embodiment of the invention, the alkylene oxide reacts with the halosilane in a similar manner to form a beta-haloalkoxy group attached directly to the silicon atom. This reaction can proceed in two ways, depending upon the amount of diepoxide employed. Thus, where the amount of the diepoxide is less than two epoxide equivalents, the reaction proceeds as follows:

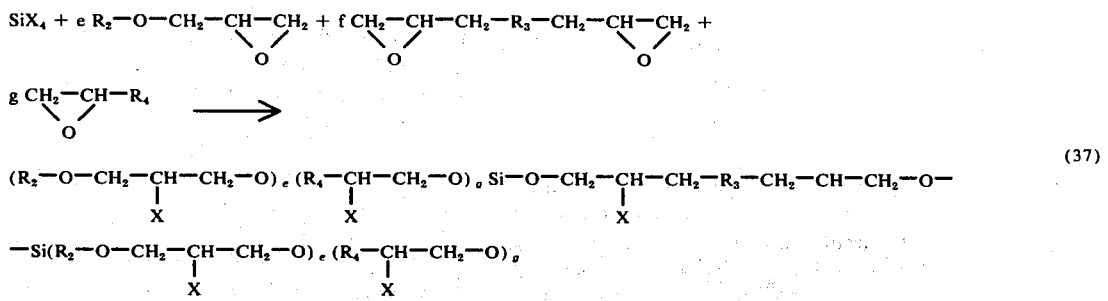

(37)

where $e$ and $g$ are each integers from 1 to 2 and $f$ is 1, and $R_4$ is hydrogen or $C_1$ to $C_6$ alkyl (e.g., methyl, ethyl, propyl, etc.).

As with the embodiment described above, the reaction product of the above is a mixture which can be used as such or, if desired, the predominant compounds having the formula stated above can be separated from the reaction mixture.

Another group of compounds which can be employed in the practice of the invention include compounds prepared by reaction of substantially stoichiometric amounts of a silicon tetrahalide and an epoxide (9) as described above, preferably an epoxide containing ethylenic unsaturation. Preferred epoxides are those of the formula

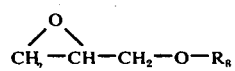
(38)

where $R_8$ is $C_2$ to $C_8$ alkenyl (e.g., alkyl, vinyl, etc.), or a group

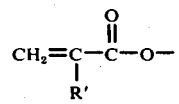
(39)

wherein R' is as described above.

These compounds have the formula

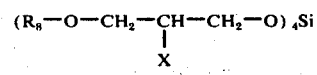
(40)

Representative compounds include the following

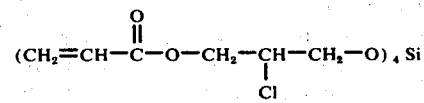
(41)

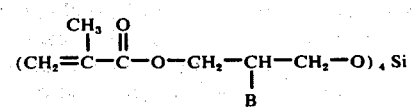
(42)

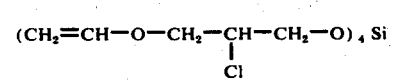
(43)

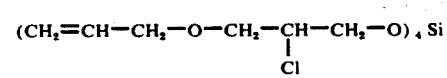
(44)

The combination of the epoxy silane and the betahaloalkoxy organo silicon compounds is formulated into a size composition for application to the glass fibers. The size composition is formulated with a solvent or diluent such as an inert organic solvent or with water. For reasons of economy, water is frequently preferred but volatile organic solvents may also be employed if desired; suitable solvents include aliphatic aldehydes, aliphatic ketones, alcohols, etc.

The relative proportions of the epoxy silane and the beta-haloalkoxy organo silicon compound can be varied within fairly wide ranges. Best results are usually obtained when the epoxy silane constitutes from 0.05 to 2% by weight of the size composition and the beta-haloalkoxy organo silicon compound constitutes 0.5 to 3% by weight of the size composition. It has been found that the weight ratio of the epoxy silane to the beta-haloalkoxy organo silicon compound is within the range of 0.05 to 1, and preferably 0.1 to 0.7. Since the epoxy silane is the more expensive component, the amount of the beta-haloalkoxy organo compound usually exceeds the amount of the epoxy silane on a weight basis.

While it is not essential to the practice of the invention, it is frequently preferred to formulate the size composition to include a film-forming material. A variety of film-forming materials can be used for this purpose, including polyester resins, polyamide resins, polyolefin resins (e.g., polyethylene, polypropylene, etc.), polyepoxide resins, vinyl resins (e.g., polyvinyl chloride, polyvinyl acetate, polyvinyl alcohol, polyvinyl pyrrolidone, etc.), waxes, polybutadienes, partially dextrinized starches and others. Such film forming materials are themselves well known to those skilled in the art and are described in U.S. Pat. Nos. 2,931,739, 2,958,114, 3,040,413, 2,252,278, 3,424,608. Combinations of two or more of such film-forming materials can also be used.

The size composition employed in the practice of this invention can also be formulated to include any of a variety of wetting agents, glass fiber lubricants, etc., also well known to the art.

The resulting size composition can be used in the treatment of glass fibers for use as reinforcement of thermosetting and for thermoplastic resins as well as elastomeric materials in accordance with conventional techniques. It has been found that the combination of the epoxy silanes and the betahaloalkoxy organo silicon compounds containing ethylenic unsaturation are particularly well suited for use as a size for glass fibers for reinforcement of polyepoxide resins.

Having described the basic concepts of the invention, reference is now made to the following examples which are provided by way of illustration and not be way of limitation of the practice of the invention in the formulation of size compositions and the use of such compositions in the treatment of glass fibers.

EXAMPLE 1

Into a 1-liter, round bottom flask equipped with a stir bar, thermometer, reflux condenser and addition funnel, there is added 280.6 cc (2.48 mole) of $SiCl_4$. Then, there is added with stirring and cooling 519.4 cc of propylene oxide followed by 862 g (4.94 epoxide equivalents) of DER 332.

The reaction mixture is stirred overnight, and analysis reveals a mixture of compounds including the compound

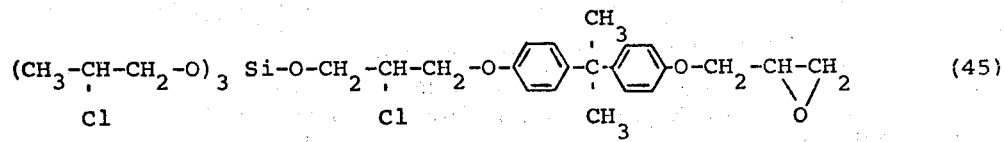
(45)

EXAMPLE 2

Using the procedure described in Example 1, 3 moles of propylene oxide is reacted with 1 mole of $SiCl_4$, and the product of the reaction in turn is reacted with one epoxide equivalent of DER 332.

Analysis reveals a mixture of compounds, including the compound $$(CH_3-\underset{Cl}{CH}-CH_2-O)_3Si-O-CH_2-\underset{Cl}{CH}-CH_2-O-\underset{}{\bigcirc}-\underset{CH_3}{\overset{CH_3}{C}}-\bigcirc-O-CH_2-\underset{Cl}{CH}-CH_2-O- \quad (46)$$

$$Si(O-CH_2-\underset{Cl}{CH}-CH_3)_3$$

EXAMPLE 3

One mole of $SiCl_4$ is reacted with 2.5 moles of propylene oxide, and the product is reacted with 0.5 moles of Epoxide No. 7 and 1.0 epoxy equivalent of ERE 1359. The product is a mixture which contains the compound

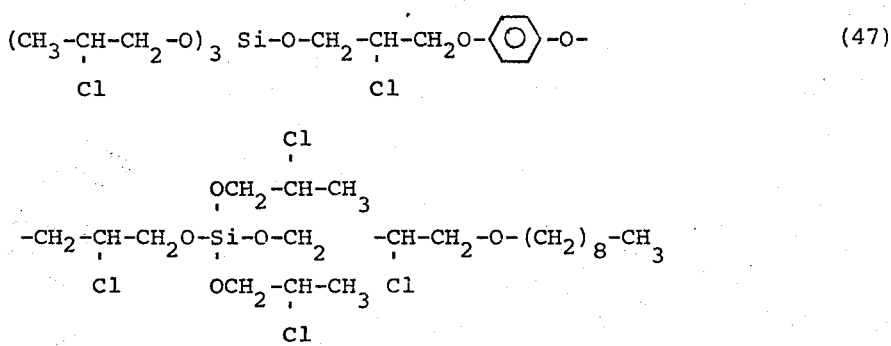

(47)

EXAMPLE 4

Each of the foregoing reaction products of Examples 1 to 3 is tested in a size composition with gamma-glycidoxypropyltrimethoxy silane (A-187 from Union Carbide).

The size compositions were formulated as follows

| Test Size A | | |
|---|---|---|
| Polyepoxide-amine resin | 1.5 | % |
| Acetic Acid | 0.13 | % |
| A-187 | 0.2 | % |
| Reaction product of Example 1 | 0.83 | % |
| Emulsifying agent (Triton X-100) | 0.083 | % |
| Water to 100% | | |
| Test Size B | | |
| Polyepoxide-amine resin | 1.5 | % |
| Acetic Acid | 0.13 | % |
| A-187 | 0.2 | % |
| Reaction product of Example 2 | 0.436 | % |
| Emulsifying agent (Triton X-100) | 0.044 | % |
| Water to 100% | | |
| Test Size C | | |
| Polepoxide-amine resin | 1.5 | % |
| Acetic acid | 0.13 | % |
| A-187 | 0.2 | % |
| Reaction product of Example 3 | 0.363 | % |
| Emulsifying agent (Triton X-100) | 0.036 | % |
| Water to 100% | | |

The polyepoxide-amine resin is a polyepoxide film former, and is described in U.S. Pat. No. 3,449,281.

Each of the test size compositions A,B and C is applied to glass fibers as they are formed in the same manner. The coated glass fibers (in the form of slivers) are employed as reinforcement in standard polyepoxide test rods, which are then tested to determine their strength, in a dry state and after having been contacted with boiling water for 24 hours. A control size was also tested in the same manner; it was formulated

| Control Size | |
|---|---|
| Polyepoxide-amine resin | 1.5% |
| Acetic acid | 0.13% |
| A-187 | 0.4% |
| Water to 100% | |

In each of test sizes A, B and C, half of the A-187 is replaced by an equivalent molar amount of the reaction products of each of Examples 1 to 3.

The results of the tests are shown in the following table:

Table I

| Silane A-187 | B-haloalkoxy compound | Dry shear strength psi ×10³ | Wet shear strength psi ×10³ |
|---|---|---|---|
| 0.4% A-187 | — | 8.52 | 6.50 |
| 0.2% A-187 | 0.83% Ex. 1 | 9.27 | 7.73 |
| 0.2% A-187 | 0.436% Ex. 2 | 8.18 | 6.56 |
| 0.2% A-187 | 0.363% Ex. 3 | 10.12 | 8.27 |

As shown by the foregoing data, the use of β-haloalkoxy compounds in combination with A-187 is at least equal to A-187 alone, and generally superior thereto, as coupling agents for bonding glass fibers to polyepoxide plastics.

EXAMPLE 5

An organo silane is prepared by placing 127.4 g (0.75 mole) of $SiCl_4$ in a reaction flask, and then adding 87.1 g (1.5 mole) of propylene oxide and 171.1 g (1.5 mole)

of allyl glycidyl ether. The product of the reaction is found to be a mixture which includes the compound $$(CH_3-\underset{Cl}{CH}-CH_2-O)_2 Si(O-CH_2-\underset{Cl}{CH}-CH_2-O-CH_2-CH=CH_2)_2 \quad (48)$$

EXAMPLE 6

One mole of $SiCl_4$ is reacted sequentially with 2.5 moles of propylene oxide, 0.5 mole of allyl glycidyl ether and 1 epoxide equivalent of DER 332. The product is a mixture which includes the compound

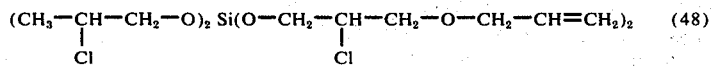 (49)

$$-CH_2-\underset{Cl}{CH}-CH_2-O-Si(O-CH_2-\underset{Cl}{CH}-CH_3)_2 (O-CH_2-\underset{Cl}{CH}-CH_2-O-CH_2-CH=CH_2)$$

EXAMPLE 7

One mole of $SiCl_4$ is reacted with 2 moles of propylene oxide and 2 moles of glycidyl acrylate. The reaction mixture produced is found to contain the compound $$(CH_3-\underset{Cl}{CH}-CH_2-O)_2 Si(O-CH_2-\underset{Cl}{CH}-CH_2-O-\overset{O}{\underset{\|}{C}}-CH=CH_2)_2 \quad (50)$$

EXAMPLE 8

One mole of $SiCl_4$ is reacted with 3 moles of propylene oxide and 1 mole of glycidyl acrylate. The product, a mixture, contains the compound $$(CH_3-\underset{Cl}{CH}-CH_2-O)_3 Si-O-CH_2-\underset{Cl}{CH}-CH_2-O-\overset{O}{\underset{\|}{C}}-CH=CH_2 \quad (51)$$

EXAMPLE 9

Using the procedure of Example 1, 1 mole of $SiCl_4$ is reacted with 2 moles of propylene oxide, 1 mole of glycidyl methacrylate and 1 epoxy equivalent of ERE 1359. The product includes $$CH_2=\underset{CH_3}{C}-\overset{O}{\underset{\|}{C}}-O-CH_2-\underset{Cl}{CH}-CH_2-O-\underset{\underset{OCH_2-CH-CH_3}{|}}{\overset{\overset{OCH_2-\overset{Cl}{\underset{|}{CH}}-CH_3}{|}}{Si}}-O-CH_2-\underset{Cl}{CH}-CH_2-O-\text{⟨Ph⟩}-O- \quad (52)$$

$$-CH_2-\underset{Cl}{CH}-CH_2-O-\underset{\underset{OCH_2-CH-CH_3}{|}}{\overset{\overset{OCH_2-\overset{Cl}{\underset{|}{CH}}-CH_3}{|}}{Si}}-O-CH_2 \quad -\underset{Cl}{CH}-CH_2-O-\overset{O}{\underset{\|}{C}}-\underset{CH_3}{C}=CH_2$$

EXAMPLE 10

One mole of $SiCl_4$ is reacted with 2 moles of propylene oxide, 1 mole of glycidyl methacrylate and 1 epoxy equivalent of DER 332. The mixture forming the product includes the compound

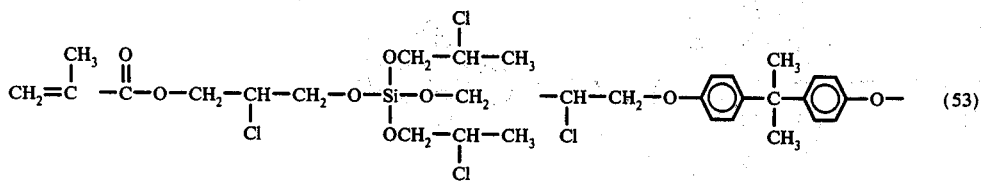
(53)

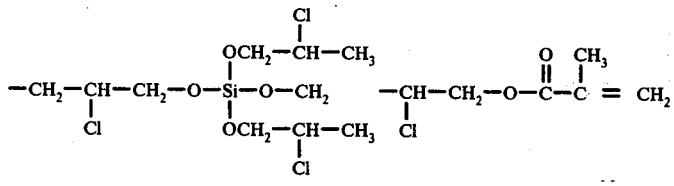

EXAMPLE 11

One mole of $SiCl_4$ is reacted with 2 moles of propylene oxide, 1 mole of glycidyl acrylate and 1 epoxy equivalent of ERE 1359. The mixture resulting includes the compound

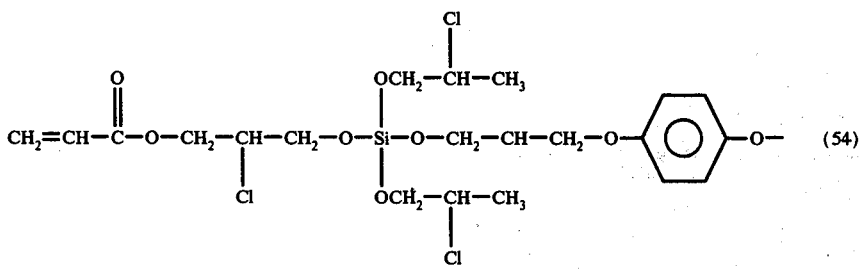
(54)

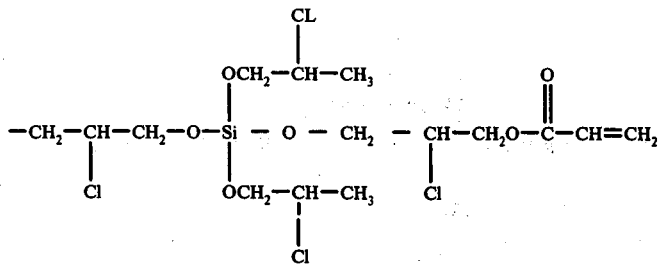

EXAMPLE 12

One mole of $SiCl_4$ is reacted with 2 moles of propylene oxide, 1 mole of allyl glycidyl ether and 1 epoxide equivalent of ERE 1359. The mixture produced includes the compound

EXAMPLE 13

One mole of $SiCl_4$ is reacted with 2 moles of propylene oxide, 1 mole of glycidyl acrylate and 1 epoxy equivalent of DER 332. The product includes the compound

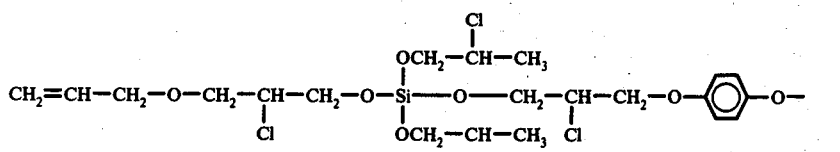
(55)

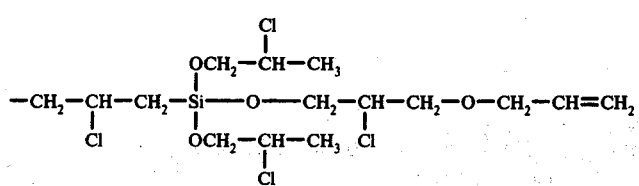

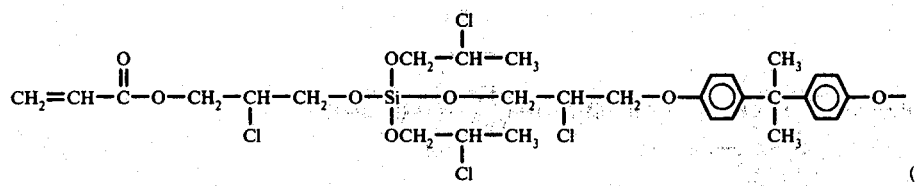

(56)

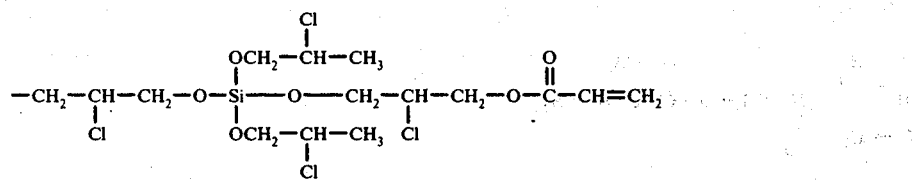

EXAMPLE 14

One mole of SiCl$_4$ is reacted with 2 moles of propylene oxide, 1 mole of glycidyl acrylate and 1 epoxide equivalent of ERL 4206. The mixture forming the product includes the compound

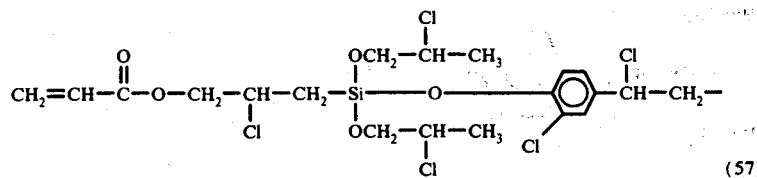

EXAMPLE 15

One mole of SiCl$_4$ is reacted with 2 moles of propylene oxide, 1 mole of allyl glycidyl ether and 1 epoxy equivalent of ERL 4206. The product includes

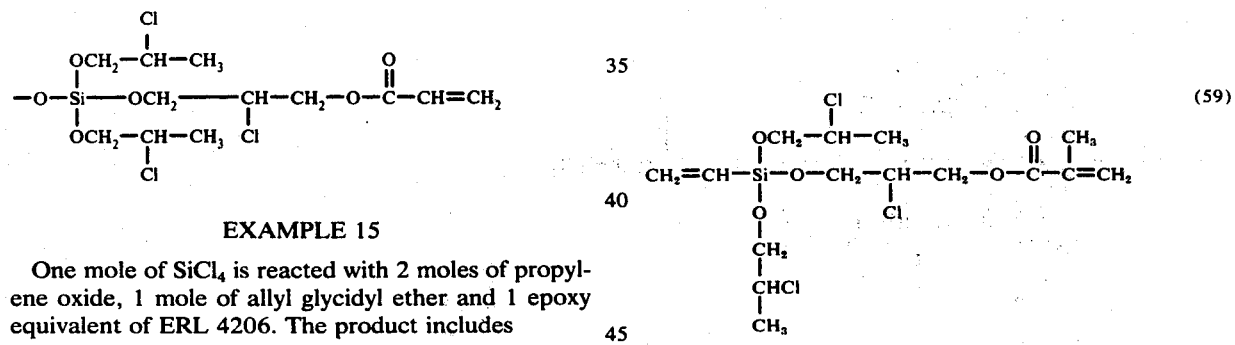

EXAMPLE 16

Using the procedure described in Example 1, one mole of vinyl trichlorosilane is reacted with 2 moles of propylene oxide and 1 mole of glycidyl methacrylate. The product of the reaction is found to contain the compound

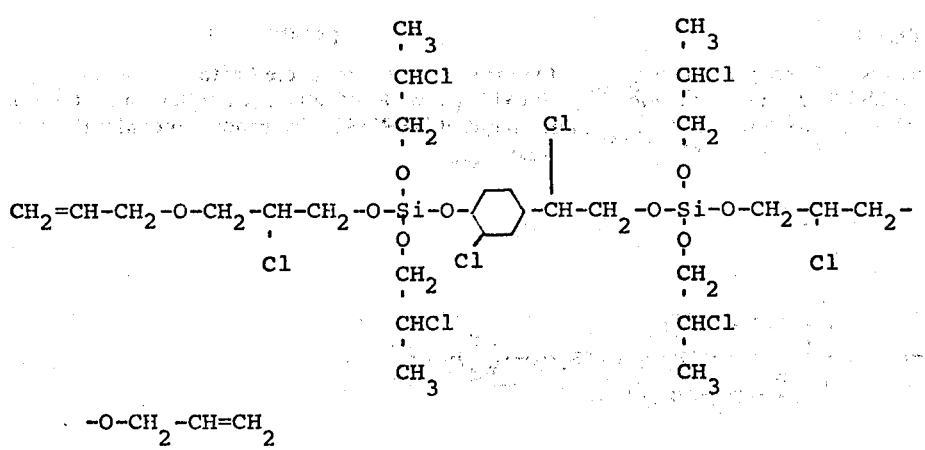

(59)

In the preparation of each of the foregoing beta-haloalkoxy compounds, the reactants are added sequentially to the SiCl$_4$ in the order indicated in each of the examples.

The reaction product is formulated into the following size composition:

| | |
|---|---|
| Reaction product of any of Examples 5–16 | 0.41% |
| Δ-glycidoxybutyltriethoxy silane | 0.25% |
| Water to 100% | |

The above composition can be applied to glass fibers to form a coating thereon as described above; the fibers are well suited for use as reinforcement for thermosetting resins.

In the final reinforced resin, the thermosetting resin constitutes a continuous phase in which the coated glass fiber reinforcements are distributed. The glass fibers can be in the form of chopped fibers, woven or non-woven mats, slivers, strands, etc. The coating on the glass fiber surfaces operates to establish a secure bonding relationship between the glass fibers and the resin.

It will be understood that various changes and modifications can be made in the details of procedure, formulation and use without departing from the spirit of the invention, especially as defined in the following claims.

We claim:

1. Glass fibers having a thin size coating thereon, said coating comprising an organo silane selected from the group consisting of a compound having the formula $$CH_2\overset{\diagdown}{\underset{O}{\diagup}}CH-CH_2-O-(CH_2)_x-Si(OR)_3$$

and a compound having the formula $$O\diagdown\text{[cyclohexane ring]}-(CH_2)_y-Si(OR)_3$$

wherein x is an integer from 3 to 6, y is an integer from 2 to 4 and R is alkyl and the hydrolysis products thereof, and an organo silicon compound prepared by reaction of (1) a halosilane selected from the group consisting of a tetrahalosilane and a halosilane of the formula $$(R_7)_nSiX_{4-n}$$

wherein $R_7$ is an organic group containing 1 to 20 carbon atoms, n is an integer from 1 to 2 and X is halogen, (2) a monoepoxide selected from the group consisting of an alkylene oxide, a functional epoxide having the formula $$CH_2\overset{\diagdown}{\underset{O}{\diagup}}CH-CH_2-O-R_2$$

wherein $R_2$ is selected from the group consisting of aryl, alkyl, alkenyl and a group having the formula $$CH_3-\underset{\underset{R'}{|}}{C}=\overset{O}{\overset{||}{C}}-$$

where R' is hydrogen or methyl, and combinations thereof, and (3) a diepoxide selected from the group consisting of an epoxide of the formula $$CH_2\overset{\diagdown}{\underset{O}{\diagup}}CH-CH_2-R_3-CH_2-CH\overset{\diagdown}{\underset{O}{\diagup}}CH_2$$

wherein $R_3$ is a divalent organic group and a cycloalkane diepoxide, with (2) being reacted in a ratio of 1 to 3 epoxide equivalents per mole of (1) and (3) being reacted in a ratio of 0.5 to 3 epoxide equivalents per mole of (1).

2. Glass fibers as defined in claim 1 wherein (2) is reacted in a ratio of at least 2.2 epoxide equivalents per mole of (1).

3. Glass fibers as defined in claim 1 wherein the halosilane is a tetrahalosilane.

4. Glass fibers as defined in claim 1 wherein the silane is a gamma-glycidoxypropyltrialkoxy silane.

5. Glass fibers as defined in claim 1 wherein (3) is a diepoxide selected from the group consisting of an epoxide having the formula $$CH_2\overset{\diagdown}{\underset{O}{\diagup}}CH-CH_2-O-\text{[phenyl]}-O-CH_2-CH\overset{\diagdown}{\underset{O}{\diagup}}CH_2$$

and an epoxide having the formula $$CH_2\overset{\diagdown}{\underset{O}{\diagup}}CH-CH_2-O-\text{[phenyl]}-\underset{\underset{CH_3}{|}}{\overset{\overset{CH_3}{|}}{C}}-\text{[phenyl]}-O-CH_2-CH\overset{\diagdown}{\underset{O}{\diagup}}CH_2$$

6. Glass fibers as defined in claim 1 wherein the coating includes a film forming material.

7. Glass fibers having a thin size coating thereon, said coating comprising an organo silane selected from the group consisting of a compound having the formula $$CH_2\overset{\diagdown}{\underset{O}{\diagup}}CH-CH_2-O-(CH_2)_x-Si(OR)_3$$

and a compound having the formula $$O\diagdown\text{[cyclohexane ring]}-(CH_2)_y-Si(OR)_3$$

wherein x is an integer from 3 to 6, y is an integer from 2 to 4 and R is alkyl and the hydrolysis products thereof, and an organo silicon compound formed by reaction of (1) a silicon tetrahalide, (2) an alkylene oxide, and (3) a diepoxide of the formula $$CH_2\overset{\diagdown}{\underset{O}{\diagup}}CH-CH_2-R_3-CH_2-CH\overset{\diagdown}{\underset{O}{\diagup}}CH_2$$

wherein $R_3$ is a divalent organic group, with (2) being reacted in a ratio of 0.5 to 2.5 epoxide equivalents per mole of the silicon tetrahalide, and (4) being reacted in a ratio of 0.5 to 3 epoxide equivalents.

8. Glass fibers as defined in claim 7 wherein the diepoxide has the formula

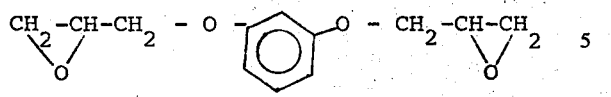

9. Glass fibers as defined in claim 7 wherein the diepoxide has the formula

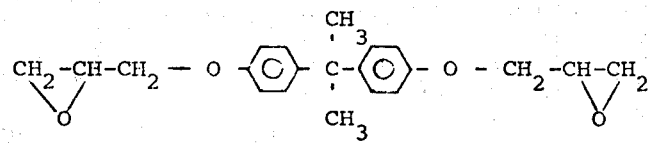

10. Glass fibers as defined in claim 7 wherein the ratio of (2) is at least 2.2 epoxide equivalents per mole of silicon tetrahalide.

11. Glass fibers as defined in claim 7 wherein the silicon tetrahalide is silicon tetrachloride.

12. Glass fibers as defined in claim 7 wherein the silane is a gamma-glycidoxypropyltrialkoxy silane.

13. Glass fibers as defined in claim 7 wherein the alkylene oxide is propylene oxide.

14. Glass fibers as defined in claim 7 wherein the coating includes a polyepoxide resin film-forming material.

15. In a glass fiber reinforced plastic material in which a thermosetting resin constitutes a continuous phase in which the glass fibers are distributed, the improvement in the bonding relationship between the glass fibers and the resin comprising glass fibers as defined in claim 1.

16. A reinforced plastic as defined in claim 15 wherein the resin is a polyepoxide resin.

17. In a glass fiber reinforced plastic material in which a thermosetting resin constitutes a continuous phase in which the glass fibers are distributed, the improvement in the bonding relationship between the glass fibers and the resin comprising glass fibers as defined in claim 7.

18. A reinforced plastic as defined in claim 17 wherein the resin is a polyepoxide resin.

19. In a glass fiber reinforced plastic material as defined in claim 17 wherein the diepoxide has the formula

20. In a glass fiber reinforced plastic material as defined in claim 17 wherein the diepoxide has the formula

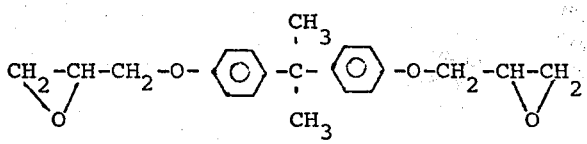

21. In a glass fiber reinforced plastic material as defined in claim 17 wherein the total of the ratios of (2) is at least 2.2 epoxide equivalents per mole of silicon tetrahalide.

22. In a glass fiber reinforced plastic material as defined in claim 17 wherein the silicon tetrahalide is silicon tetrachloride.

23. In a glass fiber reinforced plastic material as defined in claim 17 wherein the silane is a gamma-glycidoxypropyltrialkoxy silane.

24. In a glass fiber reinforced plastic material as defined in claim 17 wherein the alkylene oxide is propylene oxide.

25. Glass fibers having a thin size coating thereon, said coating comprising an organo silane selected from the group consisting of a compound having the formula

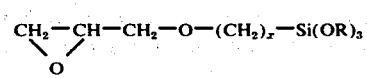

and a compound having the formula

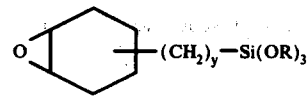

wherein x is an integer from 3 to 6, y is an integer from 2 to 4, and R is alkyl or hydrolysis products thereof, and an organo silicon compound prepared by reaction of (1) a halosilane selected from the group consisting of a tetrahalosilane and a halosilane of the formula

wherein $R_7$ is an organic group containing 1 to 20 carbon atoms, n is an integer from 1 to 2, and X is halogen, (2) an alkylene oxide and (3) a functional epoxide of the formula

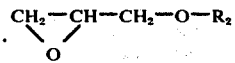

wherein $R_2$ is selected from the group consisting of aryl, alkyl, alkenyl and a group having the formula

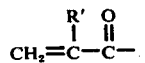

wherein R' is hydrogen or methyl, with the ratio of (2) being 1 to 3 epoxide equivalents per mole of (1) and the ratio of (3) being 0.5 to 3 epoxide equivalents per mole of (1).

26. Glass fibers as defined in claim 25 wherein (1) is a tetrahalosilane.

27. Glass fibers as defined in claim 25 wherein the functional epoxide is glycidyl acrylate or methacrylate.

28. Glass fibers as defined in claim 25 wherein the coating includes a film-forming material.

29. In a glass fiber reinforced plastic material in which a thermosetting resin constitutes a continuous phase in which the glass fibers are distributed, the improvement in the bonding relationship between the glass fibers and the resin comprising glass fibers as defined in claim 25.

30. In a reinforced plastic material as defined in claim 29 wherein the resin is a polyepoxide resin.

31. Glass fibers having a thin size coating thereon, said coating comprising an organo silane selected from the group consisting of a compound having the formula

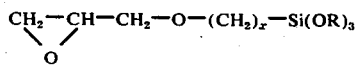

and a compound having the formula

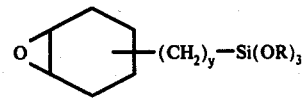

and a organo silicon compound having the formula

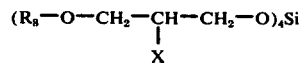

wherein $R_8$ is alkenyl or a group of the formula

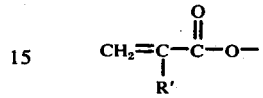

wherein R' is hydrogen or methyl, and X is halogen.

32. A glass fiber reinforced plastic product reinforced with glass fibers as defined in claim 31.